US006658081B2

United States Patent
Bruder et al.

(10) Patent No.: US 6,658,081 B2
(45) Date of Patent: Dec. 2, 2003

(54) COMPUTED TOMOGRAPHY METHOD AND APPARATUS FOR OPTIMIZED DETECTOR UTILIZATION AND DOSE UTILIZATION

(75) Inventors: Herbert Bruder, Hoechstadt (DE); Thomas Flohr, Uehlfeld (DE); Karl Stierstorfer, Erlangen (DE)

(73) Assignee: Siemens Aktiengesellschaft, Münich (DE)

( * ) Notice: Subject to any disclaimer, the term of this patent is extended or adjusted under 35 U.S.C. 154(b) by 0 days.

(21) Appl. No.: 10/164,234

(22) Filed: Jun. 5, 2002

(65) Prior Publication Data

US 2003/0068015 A1 Apr. 10, 2003

(30) Foreign Application Priority Data

Jun. 5, 2001 (DE) .......................................... 101 27 269

(51) Int. Cl.⁷ .................................................. A61B 6/03
(52) U.S. Cl. ......................................... 378/15; 378/901
(58) Field of Search ............................ 378/4, 8, 15, 19, 378/901

(56) References Cited

U.S. PATENT DOCUMENTS

| 5,802,134 | A |   | 9/1998 | Larson et al. | |
| 5,881,122 | A | * | 3/1999 | Crawford et al. | 378/4 |
| 5,887,047 | A | * | 3/1999 | Bailey et al. | 378/4 |
| 5,909,477 | A | * | 6/1999 | Crawford et al. | 378/4 |
| 6,272,200 | B1 | * | 8/2001 | Pan et al. | 378/15 |
| 6,459,754 | B1 | * | 10/2002 | Besson et al. | 378/4 |

OTHER PUBLICATIONS

"Algorithm for Image Reconstruction in Multi–Slice Helical CT," Taguchi et al, Med. Phys, 25 (4), Apr. 1998, pp. 550–561.
"Multi–Slice Helical CT: Scan and Reconstruction," Hu, Med. Phys. 26(1), Jan. 1999, pp. 5–18.
"New Efficient Fourier–Reconstruction Method for Approximate Image Reconstruction In Spiral Cone–Beam CT At Small Cone Angles," Schaller et al, SPIE Medical Imaging Conf., Proc. vol. 3032, pp. 213–224 (1997).
"Exact Radon Rebinning Algorithm for the Long Object Problem in Helical Cone–Beam CT," Schaller et al, IEEE Trans. On Med. Imaging, vol. 18, No. 5 May 2000, pp. 361–375.

* cited by examiner

Primary Examiner—David V. Bruce
(74) Attorney, Agent, or Firm—Schiff Hardin & Waite

(57) ABSTRACT

In a method and apparatus for computed tomography, a subject is scanned with a conical ray beam emanating from a focus and the attenuated beam is detected with a matrix-like detector array. The focus is moved on a spiral path around a system axis relative to the subject, and the detector array supplies output data corresponding to the received radiation. The output data are supplied during the motion of the focus on a spiral segment and have a length adequate for the reconstruction of a CT image, and are divided into output datasets with respect to sub-segments. Segment images having an inclined image plane relative to the system axis are reconstructed for the sub-segments. The segment images respectively belonging to the sub-segments are combined into a partial image with respect to a target image plane, and the partial images are combined into a resulting CT image with respect to the target image plane.

60 Claims, 5 Drawing Sheets

COMPUTED TOMOGRAPHY METHOD AND APPARATUS FOR OPTIMIZED DETECTOR UTILIZATION AND DOSE UTILIZATION

BACKGROUND OF THE INVENTION

1. Field of the Invention

The present invention is directed to a method for computed tomography (CT), of the type wherein, for scanning a subject with a conical ray beam emanating from a focus and with a matrix-like detector array for detecting the ray beam, the focus is moved on a spiral path around a system axis relative to the subject, with the detector array supplying output data corresponding to the received radiation, and wherein images having an inclined image plane relative to the system axis are reconstructed from output data supplied during the motion of the focus on a spiral segment. The invention also is directed to a computed tomography apparatus of the type having a radiation source having a focus from which a conical ray beam emanates, a matrix-like detector array for detecting the ray beam, the detector array supplying output data corresponding to the received radiation, an arrangement for generating a relative motion between radiation source and detector array, and a subject, and an image computer to which the output data are supplied, the means for generating a relative motion for scanning the subject with the ray beam and the two-dimensional detector array causing a relative motion of the focus with respect to the system, such that the focus moves on a helical spiral path relative to the system, axis having a central axis corresponding to the system axis, and whereby the image computer reconstructs images with an image plane inclined relative to the system axis from output data supplied during the motion of the focus on a spiral segment.

2. Description of the Prior Art

Various CT methods using conical x-ray beams are known particularly in conjunction with detector arrays having a number of lines of detector elements. The cone angle that thereby occurs as a consequence of the conical shape of the x-ray beam is taken into consideration in various ways.

In the simplest case (see, for example, K. Taguchi, H. Aradate, "Algorithm for image reconstruction in multi-slice helical CT", Med. Phys. 25, pp. 550–561, 1998; H. Hu, "Multi-slice helical CT: Scan and reconstruction", Med. Phys. 26, pp. 5–18, 1999), the cone angle is left out of consideration, with the disadvantage that artifacts occur in a large number of lines, and thus a large cone angle.

Further, an algorithm referred to as the MFR Algorithm (S. Schaller, T. Flohr, P. Steffen, "New, efficient Fourier-reconstruction method for approximate image reconstruction in spiral cone-beam CT at small cone-angles", SPIE Medical Imaging Conf., Proc. Vol. 3032, pp. 213–224, 1997) is known, the disadvantage thereof being that a complicated Fourier reconstruction was necessary and the image quality leaves much to be desired.

Exact algorithms (for example, S. Schaller, F. Noo, F. Sauer, K. C. Tam, G. Lauritsch, T. Flohr, "Exact Radon rebinning algorithm for the long object problem in helical cone-beam CT, in Proc. of the 1999 Int. Meeting on Fully 3D Image Reconstruction, pp. 11–14, 1999 or H. Kudo, F. Noo and M. Defrise,:Cone-beam filtered back-projection algorithm for truncated helical data", in Phs. Med. Biol., 43, pp. 2885–2909, 1998) have also been described, which have the common disadvantage of extremely complicated reconstruction.

A method and CT apparatus of the type initially described are disclosed in U.S. Pat. No. 5,802,134. In accord therewith, in contrast, images are reconstructed for image planes that are inclined by an inclination angle $\gamma$ around the x-axis relative to the system axis z. As a result, the (at least theoretical) advantage is achieved that the images contain fewer artifacts when the inclination angle $\gamma$ is selected such that a good and optimum adaptation of the image plane to the spiral path is established, insofar as possible according to a suitable error criterion, for example minimum square average of the distance measured in z-direction of all points of the spiral segment from the image plane.

In U.S. Pat. No. 5,802,134, fan data, i.e. data registered in the known fan geometry are employed for the reconstruction, the data having been acquired with the motion of the focus along a spiral segment having the length 180° plus the fan angle, for example 240°. The optimum inclination angle $\gamma$ is dependent on the slope of the spiral, and thus on the pitch p.

Fundamentally, the method disclosed in U.S. Pat. No. 5,802,134 can be employed for arbitrary values of the pitch p. However, an optimum utilization of the detector area available, and thus of the radiation dose applied to the patient for image acquisition (dose utilization) is not possible below the maximum pitch $P_{max}$. This is because even though a given transverse slice, i.e. a slice of the subject residing at a right angle relative to the system axis z, is scanned via a spiral segment that is longer then 180° plus fan angle, only a spiral segment having the length 180° plus the cone angle can be utilized for values of the pitch p below the maximum pitch $P_{max}$ since the utilization of a longer spiral segment would make it impossible to adapt the image plane to the spiral path well enough.

SUMMARY OF THE INVENTION

An object of the present invention is to provide a method and a CT apparatus of the type initially described wherein the cone angle is taken into consideration and wherein the preconditions for an optimum detector utilization and thus an optimum dose utilization are also established for values of the pitch p below the maximum pitch $P_{max}$.

This object is achieved in accordance with the invention in a method for producing a computed tomography image wherein a subject is scanned with a conical x-ray beam emanating from a focus which is detected, after attenuation by the subject, using a matrix-like detector array while the focus moves along a spiral path around the subject relative to a system axis. The detector array generates output data dependent on the radiation from the x-ray beam that is incident thereon, and the output data, for a segment of the spiral path having a length that is adequate for reconstructing a CT image, are divided into a number of datasets respectively for a number of sub-segments of the aforementioned segment. Each of these sub-segments has a length that is shorter than the length that is adequate for reconstructing a CT image. For each of the sub-segments, a number of segment images is reconstructed, the segment images being in respective planes that are inclined relative to the system axis. For each sub-segment, the segment images associated therewith are combined to form a partial image with respect to a target image plane. These partial images that arise for the respective sub-segments are then combined to form a resulting CT image with respect to the target plane.

Since in the inventive method, the spiral segment whose length suffices for the reconstruction of a CT image is divided into sub-segments whose lengths are each less then the length required for the reconstruction of a CT image, the deviations of the image planes of the segment images reconstructed with respect to the sub-segments from the spiral path along the sub-segments are very small. The segment images thus contain only very slight errors caused by deviations of the image planes of the segment images from the spiral path along the sub-segments, so that the image quality in the generation of the resulting CT image is high.

The maximum inclination of the image planes of the segment images is defined from the condition that rays for the image plane of the respective segment image must be present at both ends of the sub-segment within the measurement field.

The segment images that are not useable by themselves because the length of the sub-segments is shorter then the length required for the reconstruction of a CT image are calculated in a known way, i.e. the rays most beneficial for the image plane of the respective segment image are selected from the projections for the respective sub-segment present in parallel or fan geometry according to a suitable error criterion, and are filtered and back-projected or reconstructed with other standard methods.

The combining of the segment images belonging to a sub-segment, i.e. their reformatting onto a target image plane, leads to a sub-image that is likewise not useable by itself because of the excessively short length of the sub-segment. It is only when the sub-images of all sub-images belonging to the respective spiral segment for the desired target image plane are combined to form a resulting CT image does a useable image arise, since the overall length of the spiral segment derived from the sub-segments suffices for the reconstruction of a CT image.

The image quality of this image is especially high when the segment images are reconstructed for image planes that are inclined around a first axis intersecting the system axis at a right angle by an inclination angle $\chi$ as well as around a second axis intersecting each of the first and the system axis at a right angle by a tilt angle $\delta$ with respect to the system axis because the adaptation of the image planes of the segment to the spiral path of the respective sub-segment is then better again.

In an embodiment of the invention, the neighboring sub-segments overlap, so the output data belonging to the overlap regions are respectively weighted such that the weights of output data corresponding to one another in the overlapping sub-segments produce a value of one.

The advantage of overlapping sub-segments is that artifacts that would otherwise occur at the adjoining edges of the sub-segments are avoided.

In an embodiment, segment images for a number $n_{ima}$ of inclined image planes are reconstructed for each sub-segment, whereby the image planes have different z-positions $z_{ima}$. Due to the reconstruction of a number of segment images having differently inclined image plane for different z-positions, it is possible—by a suitable selection of the inclination angle $\gamma$ and of the tilt angle $\Delta$—to optimally adapt the image plane of the respective segment image for each of these z-positions to the sub-segment and to thus utilize the detector array as well as the dose completely in theoretical terms and to the greatest extent in practice. In a preferred embodiment of the invention, the number of inclined image planes intersect in a straight line that proceeds tangentially relative to the sub-segment.

In order to obtain an optimally complete detector utilization and dose utilization, the following applies according to a version of the invention for the extreme values $+\delta_{max}$ and $-\delta_{max}$ of the tilt angle $\delta$ of the inclined image planes belonging to a sub-segment:

$$\pm \delta_{\max} = \arctan\left(\frac{\frac{WM}{2} + Sp\frac{\alpha_1}{2\pi} \pm RFOV\cos\alpha_1\tan\gamma_0}{-\frac{R_f}{\cos\gamma_0} - (\pm RFOV)\frac{\sin\alpha_1}{\cos\gamma_0}}\right)$$

wherein $\gamma_0$ is the value of the inclination angle $\gamma$ determined for the tilt angle $\delta=0$ according to $$\gamma_0 = \tan\left(\frac{-Sp\hat{\alpha}}{2\pi R_f \sin\hat{\alpha}}\right)$$

For a high image quality, in another version of the invention the optimum value $\gamma_{min}$ of the inclination angle belonging to a given amount $|\delta_{max}|$ of the maximum value of the tilt angle $\delta$ is determined such that an error criterion is met, for example minimum average of the squares of the respective spacings of all points of the sub-segment from the image plane measured in the z-direction, is met.

If the rotational axis, around which the focus rotates around the system axis, is not identical with the system axis but intersects the system axis at an angle referred to as a gantry angle $\rho$, then the following applies to the inclination angle $\gamma'$ to be selected:

$$\gamma' = \arctan\frac{Sp \cdot \cos\rho}{\sqrt{4\pi^2 \cdot R_f + S^2 P^2 + 4\pi \cdot R_f \cos\alpha \sin\rho \cdot Sp}}$$

Here, as well, there is the possibility of determining the appertaining optimum value of the inclination angle $\gamma'$ for a given magnitude of the maximum value of the tilt angle $|\delta_{max}|$ such that an error criterion, for example minimum average of the squares of the respective spacings of all points of the sub-segment from the image plane measured in the z-direction.

In order to obtain an optimally complete detector and dose utilization, the following is also valid according to a version of the invention for the number $n_{ima}$ of the inclined image planes, for which segment images with inclined plane are generated for each sub-segment:

$$n_{ima} = \text{floor}\left[\frac{sM}{p}\right]$$

wherein s is the length of the sub-segments.

Likewise for an optimally complete detector and dose utilization, the tilt angles $\delta$ of the inclined image planes are determined in a version of the invention according to $$\delta(i) = \delta_{\max}\frac{2i - (n_{ima} - 1)}{n_{ima} - 1}$$

given the condition of detector lines of equal width.

In order to create the conditions for obtaining transverse tomograms to which the users of CT apparatus are accustomed, a reformatting is provided according to one version of the invention, i.e. a sub-image is generated in a further method wherein a number of segment images are combined. In an embodiment of the invention, it may occur that a number of segment images are combined to form a sub-image by interpolation or by, in particular, weighted averaging.

The reconstruction slice thickness of the sub-images, and thus of the resulting CT image is set according to a preferred embodiment of the invention by weighting the segment images according to the desired reconstruction slice thickness of the sub-image in the combining to form a sub-image.

In the combination of a number of segment images to form a sub-image, there is the possibility according to a preferred version of the invention of selecting the number of segment images that are combined for generating a sub-image according to the desired reconstruction slice thickness of the sub-image. For an optimally high image quality, there is the possibility of reconstructing the segment images with the least possible slice thickness.

A desired reconstruction slice thickness of a sub-image can be set according to another preferred version of the invention by selecting the number of segment images for generating a sub-image according to the following equation:

$$N_M = 2 \cdot \max(z^*, \sup_{\phi \Delta \geq R}) / W \cdot N_S$$

The combining of the sub-images into the resulting CT image preferably ensues by addition, also preferably for a target image plane that intersects the system axis at a right angle. The target image plane, however, also can be inclined relative to the system axis.

In order to keep the amount of data arising in the generation of the segment images within limits, in a version of the invention the data corresponding to the segment images are compressed.

In a preferred embodiment of the invention the compressed data corresponding to the segment images exhibit a non-uniform pixel matrix such that the resolution in a first direction, proceeding essentially in the direction of the reference projection direction belonging to the respective sub-segment, is higher then in a second direction that proceeds essentially orthogonally relative to the reference projection direction. Such a procedure is possible because the information density and the segment images orthogonally to the reference projection direction belonging to the respective sub-segment is significantly greater than in the reference projection direction belonging to the respective sub-segment.

In a version of the invention, the realization of a non-uniform pixel matrix is especially simple when the compressed data corresponding to the segment images are pixels having an oblong shape, particularly rectangular pixels, with the longest extent of each pixel proceeding essentially in the direction of the reference projection direction belonging to the respective sub-segment.

Because it is time-saving, it is especially advantageous, according to another preferred embodiment of the invention, to reconstruct the segment images in the non-uniform pixel matrix, since significantly fewer pixels need to be reconstructed than in the case of a uniform pixel matrix that has the same resolution in the reference projection direction belonging to the respective sub-segment. The back-projection has an especially simple form when the back-projection direction essentially corresponds to the direction of the reference projection direction belonging to the respective sub-segment.

Since the resulting CT image exhibits a uniform pixel matrix in the usual way, the compression—if it is based on the employment of a non-uniform pixel matrix—must be reversed according to a version of the invention no later than during the combining of the sub-images to form the resulting CT image.

The above object also is achieved in a computed tomography apparatus operating according to the inventive CT method described above. The comments and discussion above relating to the inventive CT method apply equally to the inventive CT apparatus.

DESCRIPTION OF THE PREFERRED EMBODIMENTS

Figure 1:
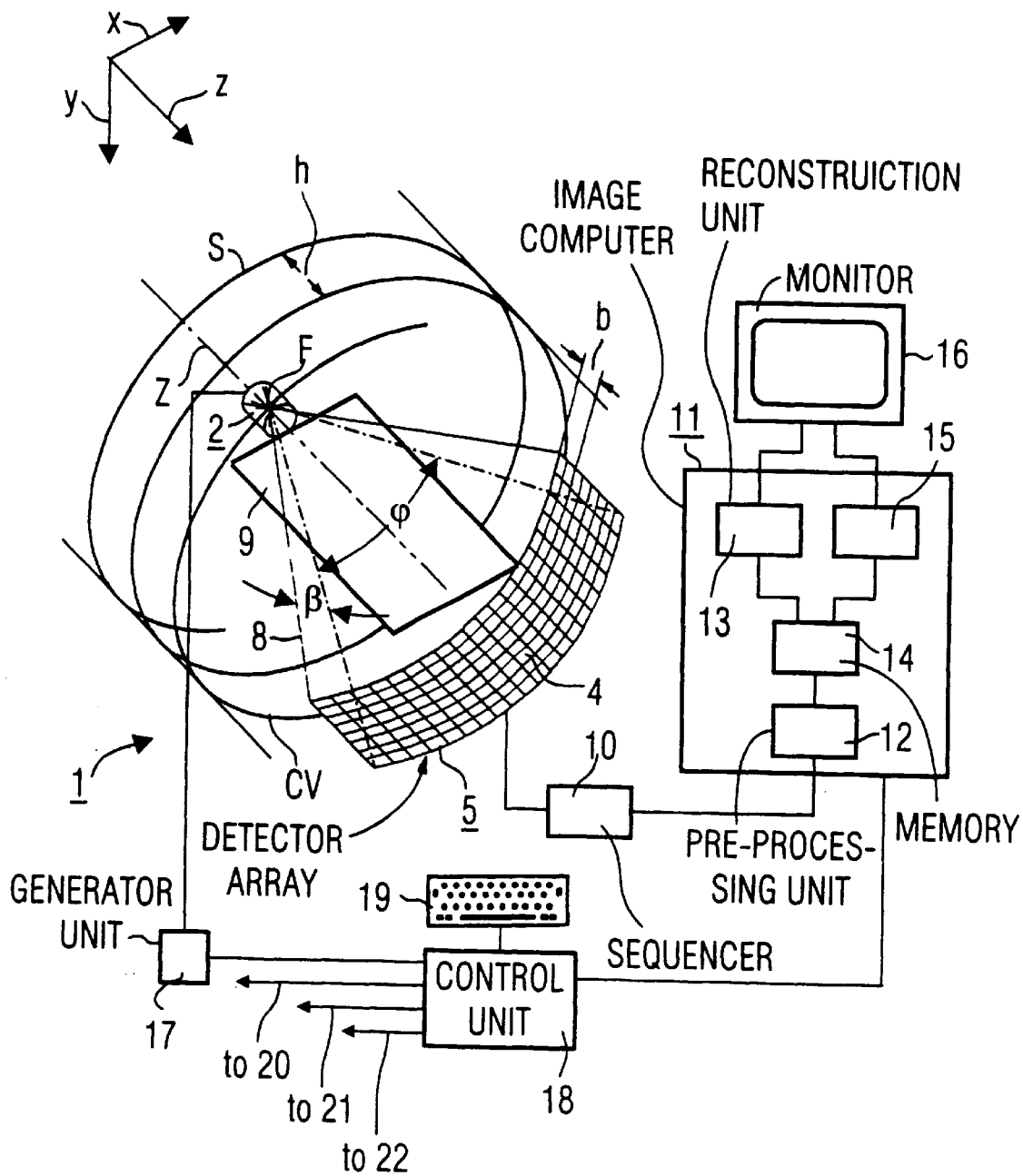
FIG. 1 is a perspective view with a block circuit diagram of a CT apparatus having multiple of lines of detector elements constructed and operating in accordance with the invention.
Figure 2:
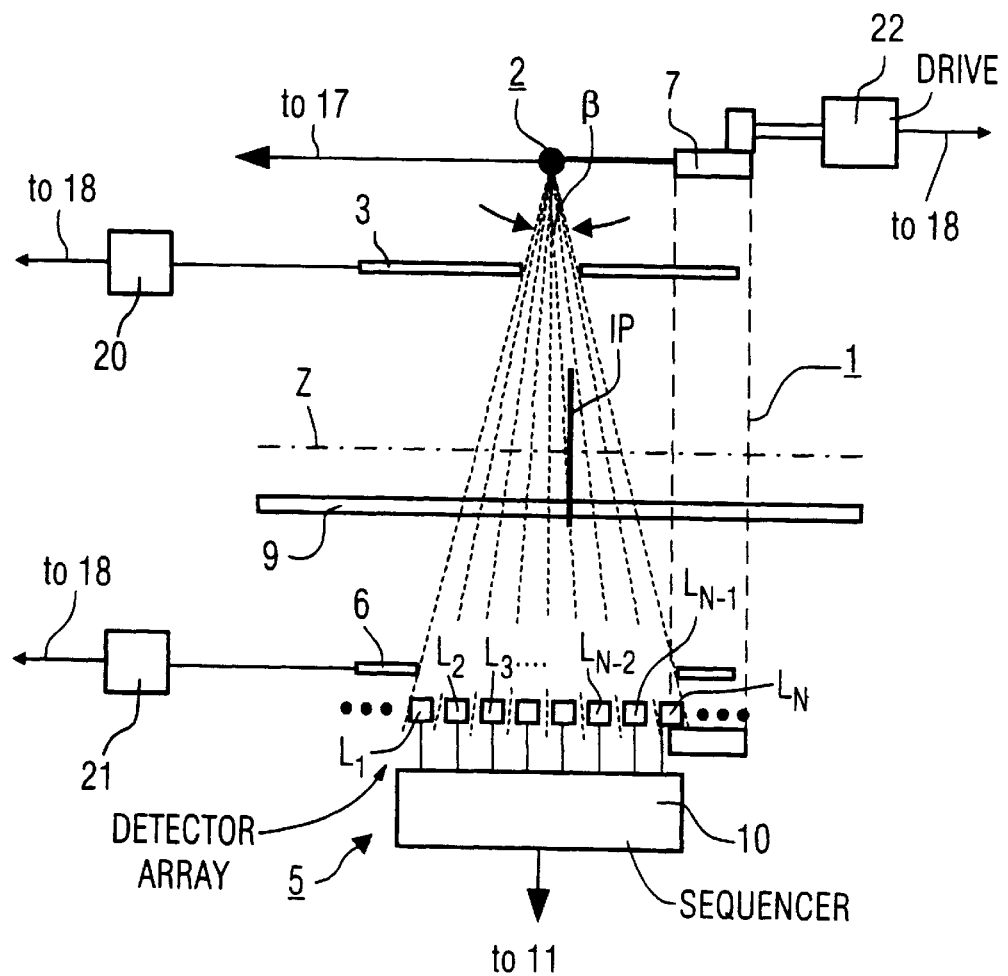
FIG. 2 is a longitudinal section through the apparatus of FIG. 1 in a first operating mode.

FIGS. 1 and 2 show a CT apparatus of the third generation suitable for the implementation of the inventive method. The measurement arrangement 1 thereof has an x-ray source 2 with a source-proximate radiation diaphragm 3 (FIG. 2) with a source-proximate radiation diaphragm 3 (FIG. 2) preceding it and a detector system 5 fashioned as a planar array of a number of rows and columns of detector elements, one of which is referenced 4 in FIG. 1. The detector system 5 has a detector-proximate radiation diaphragm 6 (FIG. 2) preceding it. For clarity, only eight lines of detector elements 4 are shown in FIG. 1; as indicated dot-dashed in FIG. 2, however, the detector system 5 has (or can have) more lines of detector elements.

Figure 3:
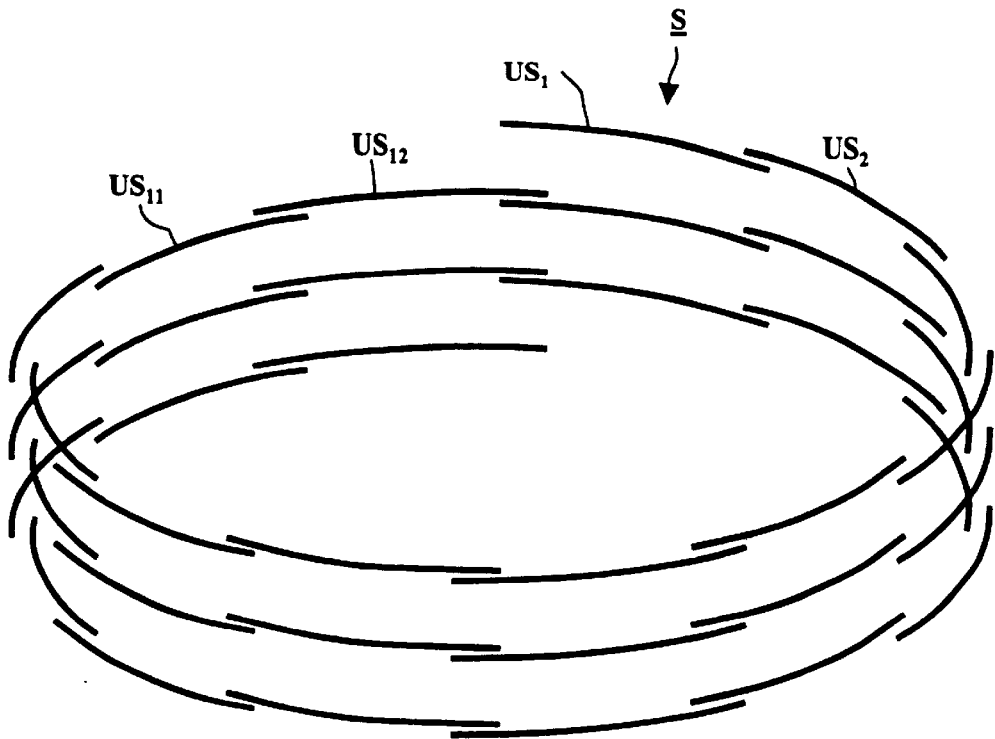
FIG. 3 illustrates the spiral path described by the focus of the x-rays in a spiral scan in the CT apparatus according to FIGS. 1 and 2.

The x-ray source 2 with the radiation diaphragm 3, and the detector system 5 with the radiation diaphragm 6, are opposite one another on a rotary frame 7 as shown in FIG. 3 such that a pyramidal x-ray beam (whose edge rays are referenced 8), that emanates from the x-ray source 2 during operation of the CT apparatus and is gated by the adjustable radiation diaphragm 3, strikes the detector system 5. The radiation diaphragm 6 is set corresponding to the cross-section of the x-ray beam that is set with the radiation diaphragm 3 so that only that region of the detector system 5 is activated that can be directly struck by the x-ray beam. In the operating mode shown in FIGS. 1 and 2, these enabled or activated lines are eight lines of detector elements 4, which are referred to as active lines below. The further lines indicated by dots are covered by the radiation diaphragm 6 and therefore are not active. Each line of detector elements 4 has a K detector element, respectively designated by a channel index k=1 through K. The active lines $L_n$ of detector elements 4 are referenced in FIG. 2 as $L_1$ through $L_N$, respectively indicated by a line index n=1 through N.

The x-ray beam exhibits the cone angle β shown in FIG. 2 which is the aperture angle of the x-ray beam in a plane containing the system axis Z and the focus F. The fan angle φ of the x-ray beam also is shown in FIGS. 1 and 2, this being the aperture angle of the x-ray beam in a plane that is oriented at a right angle relative to the system axis Z and containing the focus F.

The rotary frame 7 can be placed into rotation around the system axis Z by a drive 22. The system axis Z proceeds parallel to the z-axis of a spatial rectangular coordinate system shown in FIG. 1.

The columns of the detector system 5 likewise proceed in the direction of the z-axis, whereby the lines (rows), whose width W is measured in the direction of the z-axis and amounts, for example, to 1 mm, proceeding transversely relative to the system axis Z and the z-axis.

In order to be able to introduce an examination subject, for example a patient, into the beam path of the x-ray beam, a support mechanism 9 is displaceable parallel to the system axis Z, i.e. in the direction of the z-axis, with a synchronization between the rotational motion of the rotary frame 7 and the translational motion of the support mechanism 9 that causes the ratio of translational to rotational velocity to be constant. This ratio can be set by selecting a value for the feed h of the support mechanism 9 per revolution of the rotary frame 7.

A volume of an examination object situated on the support mechanism 9 thus can be examined during the course of a volume scan. The volume scan can be undertaken in the form of a spiral scan in the sense that, given simultaneous rotation of the measurement unit 1 and translation of the support mechanism 9, a number of projections from different projection directions is registered with the measurement unit per revolution of the measurement unit 1. In the spiral scan, the focus F of the x-ray source moves on a spiral path (referenced S in FIG. 1) relative to the support mechanism 9.

The measured data corresponding to the individual projections and read out in parallel during the spiral scan from the detector elements of every active line of the detector system 5 are subjected to a digital-to-analog conversion in a data editing unit 10, and are serialized and transmitted to an image computer 11.

After a pre-processing of the measured data in a pre-processing unit 12 of the image computer 11, the resulting data stream proceeds to a reconstruction unit 13 that reconstructs CT images of desired slices of the examination subject from the measured data, either according to methods that are known themselves (for example, 180 LI or 360 LI interpolation) or, in an operating mode corresponding to the invention, according to a method that is explained in greater detail.

The CT images are composed of pixels arranged in a matrix, with the pixels being allocated to the respective image plane. A CT number in Hounsfield units (HU) is allocated to each pixel, and the individual pixels, corresponding to a CT number/gray scale value—are presented in a gray value corresponding to the respective CT number.

The images reconstructed by the tomogram reconstruction unit 13 and the x-ray shadowgram reconstruction unit are displayed at a display unit 16, for example a monitor, connected to the image computer 11.

The x-ray source 2, for example an x-ray tube, is supplied with the necessary voltages and currents, for example the tube current U, by a generator unit 17. In order to be able to set these parameters to the necessary values, the generator unit 17 has a control unit 18 with a keyboard 19 which allows the necessary settings.

The rest of the operation and control of the CT apparatus ensues with the control unit 18 and the keyboard 19, this being illustrated by the connection of the control unit to the image computer 11.

Among other things, the number N of active lines of detector elements 4, and thus the position of the radiation diaphragms 3 and 6, can be set, for which purpose the control unit 18 is connected to adjustment units 20 and 21 allocated to the radiation diaphragms 3 and 6. Further, the rotation time τ can be set, which is time the rotary frame 7 requires for a complete revolution. This is illustrated by the connection of the drive unit 22 for the rotary frame 7 to the control unit 18.

When an operating mode in accordance with the invention is selected, the calculation of the corresponding CT images ensues using the inventive method explained in greater detail below.

To that end, a spiral scan is implemented over a length that suffices at least for the reconstruction of a CT image. In the example illustrated in FIG. 3, this is a spiral scan of the length 6π. Measured data corresponding to a number of overlapping sub-segments are obtained from the measured data thereby acquired, with the length of each sub-segment being less than the length required for the reconstruction of a CT image. The number and length, for example π/4 or π/8, of the sub-segments are selected such that they produce at least one spiral segment overall having length, for example π+φ, that suffices for the reconstruction of a CT image, i.e. it is at least equal to the length required for the reconstruction of a CT image. A number of $N_{tilt}$ of segment images, whose pixels relate to different image planes inclined relative to the middle plane, is calculated for each of the sub-segments from the corresponding measured data.

It can be seen from FIG. 3 that 12 overlapping sub-segments are present per full revolution in the described exemplary embodiment, i.e. $N_\alpha$=12. The sub-segments of the first of the three full revolutions shown in FIG. 3 are referenced $US_1$ through $US_{12}$ in FIG. 3.

Figure 4:
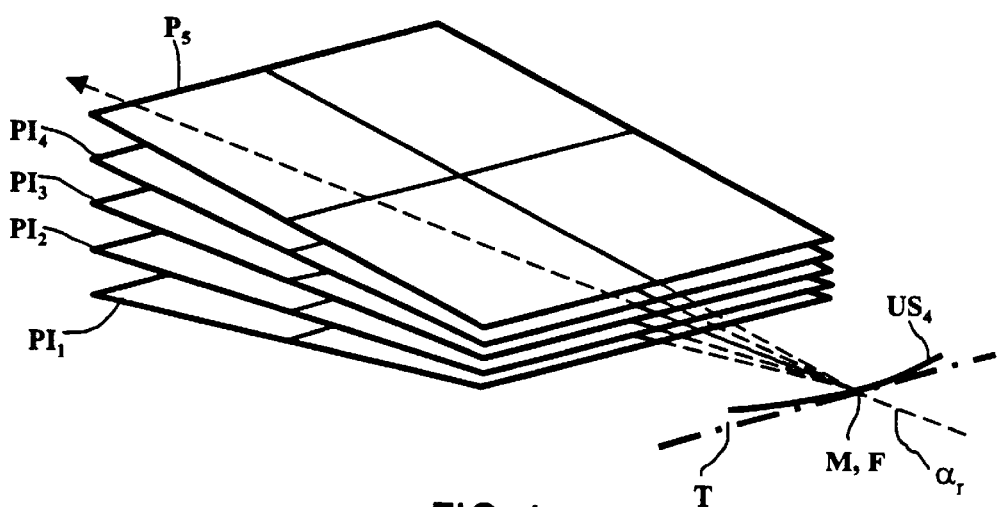
FIG. 4 illustrates the image planes of the segment images belonging to a sub-segment in accordance with the invention.

In the exemplary embodiment, five segment images are calculated per sub-segment, as can be seen from FIG. 4 with reference to the example of the sub-segment $US_4$, i.e. $N_{tilt}$=5, this being illustrated by the image planes $Pl_1$ through $Pl_5$ of the segment images.

For a full revolution, thus, a total of $N_\alpha * N_{tilt}$=60 segment images are calculated from the measured data of the full revolution, with the segment images belonging to a sub-segment being combined later to form a sub-image.

The image planes $Pl_1$ through $Pl_5$ of the segment images all intersect in a straight line according to FIG. 4. In the illustrated exemplary embodiment, this line is the tangent T at the middle M of the sub-segment in question, i.e. that point of the portion of the focal path belonging to the sub-segment that lies at half the arc length of this portion of the focal path.

Those measured values that correspond to the line integrals required for a reconstruction of the respective segment image are selected for each of these image planes $Pl_1$ through $Pl_5$ from the measured data that are supplied by the various detector lines $L_1$ through $L_8$. The selection ensues such that the beams utilized for reconstruction of the respective segment image satisfy a suitable error criterion with respect to their distance from the inclined image plane of the respective segment image. In the exemplary embodiment, this is the minimum average of the squares of the distances measured in the z-direction, of all rays utilized for the reconstruction of the respective segment image, from the respective, inclined image plane $Pl_1$ through $Pl_5$.

The maximum inclination of an image plane of a segment image thus is defined by the requirement that measured values must be available for all required line integrals whose rays lie adequately close to the inclined image plane according to the error criterion.

The segment image belonging to each image plane $Pl_1$ through $Pl_5$ is then calculated from these line integrals compiled for each image plane $Pl_1$ through $Pl_5$ from different measured values, for example by means of the standard reconstruction method of convolution and back-projection. The pixels of these segment images belong to the respective, inclined image plane $Pl_1$ through $Pl_5$. In the described exemplary embodiment, thus, a stack of five segment images is calculated for each sub-segment.

The $N_{tilt}$ segment images obtained in this way per sub-segment are combined in a following reformatting step to form a sub-image with respect to a desired target image plane IP that is different from the image planes $Pl_1$, through $Pl_5$ and intersects the system axis Z, preferably at a right angle as shown in FIG. 2, dependent on selectable combining modes (explained below) either by weighting or by interpolation. Independently of the combining mode, the image noise is reduced during the course of the combining, and the desired reconstruction slice thickness is set, with the setting of the segment images ensuing by means of the weighting and/or the number of the segment images involved in the reformatting. This number preferably equals to the number of segment images reconstructed per sub-segment.

The $N\alpha$ sub-images obtained in this way are combined with respect to the target image plane to form a resulting CT image in a final reformatting step, by addition.

The combining of segment images to form a sub-image ensues in a first combining mode by weighting, by either of two selectable weighting modes. Independently of the selected weighting mode, the pixels of the segment images respectively contribute as source pixels to a corresponding target pixel of the resulting CT image, and the magnitude of a source pixel relative to a target pixel is weighted dependent on a geometric reference quantity. In other words: the CT number belonging to a target pixel is determined from the CT numbers of the corresponding source pixels taking the geometrical reference quantity into consideration.

In the first weighting mode, the distance of the respective source pixel from the corresponding target pixel is taken into consideration as the geometrical reference quantity.

In the second weighting mode, a weighting dependent on the distance of the source pixel from the middle of the sub-segment in question additionally ensues in order to avoid artifacts.

In a second combining mode, the combining of the segment images to form a sub-image ensues by interpolation, i.e. the target pixels—the pixels of the resulting CT image—are determined by interpolation, for example linear interpolation, from the corresponding source pixels, i.e. from the corresponding pixels of the segment images.

The conditions underlying the reconstruction of segment images shall be explained as an example below on the basis of a sub-segment that is centered with respect to a reference projection angle $\alpha_r=0$. Since the image planes of the $n_{ima}$ segment images are inclined relative to the x-axis by the inclination angle $\gamma$ as well as relative to the y-axis by the tilt angle $\delta$, a normal vector of an image plane is established by:

$$\vec{n}(\gamma, \delta) = \begin{pmatrix} \sin\delta \\ -\cos\delta\sin\gamma \\ \cos\delta\cos\gamma \end{pmatrix} \quad (1)$$

The distance $d(\alpha, \delta, \gamma)$ that an arbitrary point $(X_f, Y_f, Z_f)$ on the spiral path, or the sub-segment under consideration, has from the image plane inclined by the inclination angle $\gamma$ and the tilt angle $\delta$ is established by $$d(\alpha, \delta, \gamma) = \vec{n}(\gamma, \delta) \cdot \begin{pmatrix} x_f + R_f \\ y_f \\ z_f \end{pmatrix} = \vec{n}(\gamma, \delta) \cdot \begin{pmatrix} -R_f\cos\alpha + R_f \\ -R_f\sin\alpha \\ Sp\frac{\alpha}{2\pi} \end{pmatrix} \quad (2)$$

$$= R_f(1-\cos\alpha)\sin\delta + R_f\sin\alpha\cos\delta\sin\gamma + Sp\frac{\alpha}{2\pi}\cos\delta\cos\gamma$$

It is assumed that the position $(-R_f, 0, 0)$ of the focus F lies in the image planes for the reference projection angle $\alpha_r=0$. The inclination angle $\gamma$ and the tilt angle $\delta$ of the inclined image plane must be selected such that all points of the sub-segment in question satisfy an error criterion, for example that the average of the squares of the distances in the z-direction of all points of the spiral segment from the image plane is minimized.

When it is assumed that b-t is the coordinate system x-y rotated by an angle $\alpha$-$\pi/2$ around the z-axis, then b-t is the local coordinate system for a projection having the projection angle $\alpha$.

$$x = b\sin\alpha + t\cos\alpha$$

$$y = -b\cos\alpha + t\sin\alpha \quad (3)$$

When a virtual detector array is imaged that corresponds to the projection of the detector array into a plane containing the system axis z, referred to as the virtual detector plane, then t=0 applies to the detector plane.

Each point (x,y,z) on the image plane is characterized by $$\vec{n}(\gamma, \delta) \cdot \begin{pmatrix} x + R_f \\ y \\ z \end{pmatrix} = (x + R_f)\sin\delta - y\cos\delta\sin\gamma + z\cos\delta\cos\gamma = 0 \quad (4)$$

When (3) with t=0 is introduced into (4), then the intersecting straight line of the virtual detector plane with the image plane is obtained:

$$z(b) = -R_f \frac{\tan\delta}{\cos\gamma} - b\left(\sin\alpha \frac{\tan\delta}{\cos\gamma} + \cos\alpha\tan\gamma\right) \quad (5)$$

The z-coordinate on the virtual detector plane is established by $$z_{Det}(b) = z(b) - Sp\frac{\alpha}{2\pi} = -R_f \frac{\tan\delta}{\cos\gamma} - Sp\frac{\alpha}{2\pi} - b\left(\sin\alpha \frac{\tan\delta}{\cos\gamma} + \cos\alpha\tan\gamma\right) \quad (6)$$

The inclination angle $\gamma$ is first optimized in the same way as in the case of U.S. Pat. No. 5,801,134, i.e. for the tilt angle $\delta=0$. The following is obtained as a result:

$$\tan\gamma_0 = \frac{-Sp\hat{\alpha}}{2\pi R_f \sin\hat{\alpha}}, \quad (7)$$

wherein $\hat{\alpha}$ is the angle at which the sub-segment penetrates the image plane.

The tile angle $\delta$ is optimized for the tilt angle $\gamma_0$ obtained with $\hat{\alpha}$ according to (7). The optimization criterion for the tilt angle $\delta$ is that the z-coordinate according to (6) for the detector lines $-RFOV \leq b \leq RFOV$ that limit the region of the examination subject acquired by the radiation toward the back or front in the z-direction must lie within the active detector area, i.e. within the region of the detector array 5 enabled by the radiation diaphragm 6 and struck by the radiation, also must utilize the detector area optimally well.

For the maximally possible tilt angle $\pm\delta_{max}$, the lines for $b=\pm RFOV$ established by the z-coordinate according to (6) reach the front or back end of the detector surface in the z-direction. When this occurs for the respective sub-segment for the projections at the start and end of the sub-segment, i.e. for the outermost projection angle $\pm\alpha_1$, the following applies:

$$z_{Det}(b=\pm RFOV) = \pm\frac{WM}{2}. \quad (8)$$

wherein M is the number of detector lines and W is the width of a detector line measured in the z-direction.

By introducing (5) for $\alpha=\alpha_1$ and $\gamma=\gamma_0$ into (7) and solving for $\delta_{max}$, the following results:

$$\tan\delta_{max} = \frac{\frac{WM}{2} + Sp\frac{\alpha}{2\pi} \pm RFOV\cos\alpha_1\tan\gamma_0}{-\frac{R_f}{\cos\gamma_0} - (\pm RFOV)\sin\frac{\alpha_1}{\cos\gamma_0}} \text{ or} \quad (9)$$

$$\pm\delta_{max} = \arctan\left(\frac{-\frac{WM}{2} + Sp\frac{\alpha_1}{2\pi} \pm RFOV\cos\alpha_1\tan\gamma_0}{-\frac{R_f}{\cos\gamma_0} - (\pm RFOV)\frac{\sin\alpha_1}{\cos\gamma_0}}\right)$$

A new $\delta_{min}$ is determined for the corresponding $\delta_{max}$ by iteration, namely by minimizing the average of the squares of the distances $d(\alpha,\delta_{max},\gamma)$ in the z-direction of all points of the sub-segment from the image plane according to (2).

The range $[-\delta_{max},\delta_{max}]$ of the tilt angle that is available is now uniformly subdivided according to the number $n_{ima}$ of the segment images to be reconstructed, preferably as in the case of the described exemplary embodiment. This means that given a uniform subdivision, each image plane $0 \leq i \leq n_{ima}-1$ is characterized by the inclination angle $Y_{min}$ (that, as in the case of the described exemplary embodiment, is preferably the same for all image planes) and by the respective tilt angle $\delta_{(i)}$, with the following being applicable for the respective tilt angle:

$$\delta(i) = \delta_{max}\frac{2i-(n_{ima}-1)}{n_{ima}-1} \quad (10)$$

The number $n_{ima}$ of the segment images to be reconstructed for the sub-segment is established by $$n_{ima} = \text{floor}\left[\frac{sM}{p}\right]. \quad (11)$$

wherein s is the arc length of the spiral path S for the sub-segment under consideration.

The reformatting occurs using interpolation functions of a selectable width, as a result of which the slice sensitivity profile and the image noise in the resulting transverse tomogram can be influenced. It is advantageous that the definition of the desired reconstruction slice thickness of the sub-images, and thus of the resulting CT images, ensues retrospectively during the course of the reformatting.

The plurality of segment images required in the reformatting to be implemented for the acquisition of a sub-images is obtained in the following way:

At the edge of the object cylinder parameterized by $(x,y)=(R_M\cos\phi, R_M\sin(\phi))$, the distance AZR of an image plane inclined by the inclination angle and the tile angle with the normal vector $$\vec{n}(\gamma,\delta) = \begin{pmatrix} \sin\delta \\ -\cos\delta\sin\gamma \\ \cos\delta\cos\gamma \end{pmatrix}$$

and with the zero point in the point $(-R_f, 0, Z_r)$, is obtained by inserting $(x,y,\Delta Z_R)$ is inserted into the plane equation $\vec{n}(\delta,\gamma)\cdot\vec{x}=0$.

The following then results:

$$\Delta z_R = -\frac{\tan(\delta)}{\cos(\gamma)}\cdot(-R_f + R_M\cdot\cos(\Phi)) + \tan(\gamma)\cdot R_M\cdot\sin(\Phi).$$

For the reformatting of a transverse tomogram with the image plane in $Z_R$, accordingly, all segment images reconstructed in the interval $$[((z_R-sup_\phi\Delta Z_R(\Phi,\delta))),((z_R+sup_\Phi\Delta z_R(\Phi,\delta)))] \quad (13)$$

must be available, i.e. must be stored in the memory 14.

When an interpolation function whose length z* exceeds the limits placed by the above interval is employed in the reformatting, then the number of segment images required for the reformatting is defined by the length of the interpolation filter.

In the general case, the following is valid for the number NM of the reconstructed images with inclined image plane required for the reformatting of a sub-image:

$$N_M = 2\cdot\max(z^*, sup_\phi\Delta z_R)/W\cdot N_S \quad (14)$$

$N_s$ is the number of segment images reconstructed per width W of a line of detector elements.

As a result of the fact that the reconstruction slice thickness of a desired sub-tomogram is retrospectively defined, the reconstruction of the segment images preferably ensues by selecting a correspondingly narrow weighting function with the least possible reconstruction slice thickness. This assures utmost sharpness in the z-direction not only of the segment images but also of the sub-images obtained by the reformatting as well as of the CT image acquired therefrom.

In addition to this advantage, the following are further advantages of the described reformatting:

The reconstruction slice thickness can be retrospectively selected without a renewed reconstruction being required;

The reconstruction slice thickness is freely selectable; and

A number of suitable interpolation functions having a freely selectable width is available for the reformatting.

Figure 5:
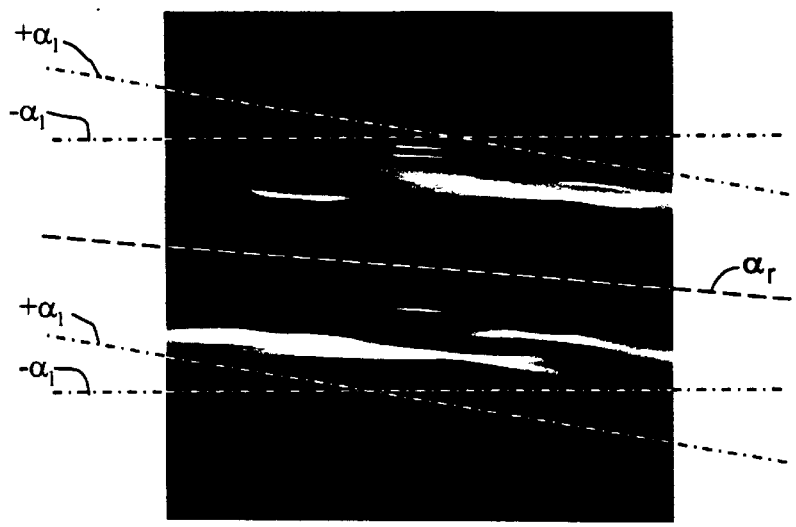
FIG. 5 illustrates an example of a segment image in accordance with the invention.

FIG. 5 illustrates the segment image belonging to the image plane $Pl_3$ as an of example from among the segment images belonging to the sub-segment $US_4$. The reference projection angle $\alpha_r$ and the outermost projection angles $+\alpha_1$ and $-\alpha_1$ belonging thereto are indicated with broken lines. It can be seen that the information density in the segment images that are orthogonal relative to the projection direction corresponding to the respective reference projection angle (referred to below as the reference projection direction) is significantly greater than in the reference projection direction.

There is therefore the possibility of compressing the data corresponding to the segment images. In the described exemplary embodiment and as a result of the fact that the data redundancy would be extremely high for the aforementioned reasons when employing a uniform pixel matrix, the data compression occurs in that the compressed data corresponding to the segment images has such a non-uniform pixel matrix corresponding to the data structure that the resolution $R_r$ in reference projection direction is less then the resolution $R_{or}$ orthogonally relative to the reference projection direction. When a given resolution orthogonally relative to the reference projection direction is assumed, then the compression factor that can be achieved in the compression corresponds to the quotient $R_{or}/R_r$.

Figure 6:
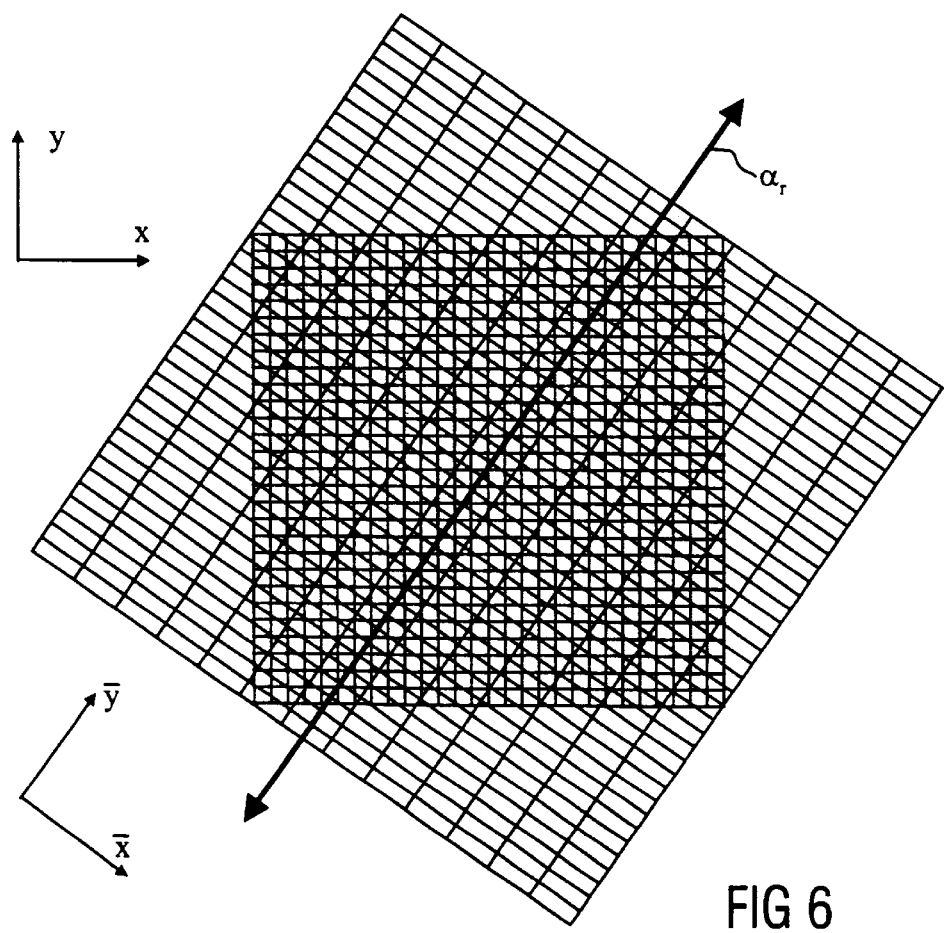
FIG. 6 illustrates the non-uniform pixel matrix of a segment image and the uniform pixel matrix of the appertaining sub-image in accordance with the invention.

In the described exemplary embodiment, the non-uniform pixel matrix is realized according to FIG. 6 wherein it can be seen that the compressed data corresponding to the segment images are represented as pixels having an oblong, shape, such as a rectangular shape, with the longest extent of the pixels proceeding in the reference projection direction.

If it is desired to reduce the memory space required for storing the segment images, a first compression operating mode is selected wherein the segment images are converted into the non-uniform pixel matrix after the reconstruction has ensued.

If it is also desired to reduce the calculating outlay required for the reconstruction of the segment images, a second compression operating mode is selected wherein the segment images are already reconstructed in the non-uniform pixel matrix. This offers the advantage that significantly fewer pixels need to be reconstructed than in the case of a uniform matrix that exhibits the same resolution orthogonally to the reference projection direction as the non-uniform pixel matrix.

During the course of the reconstruction in the non-uniform matrix, the coordinate system with the axis and the axis underlying the back-projection is rotated according to FIG. 5 such that the back-projection direction corresponds to the respective reference projection direction.

Regardless of which of the two compression operating modes is selected, the data compression must in turn be canceled no later than during the combining of the sub-images to form a resulting CT image. Therefore in the inventive CT apparatus the sub-images are also generated on the basis of the non-uniform pixel matrix, and the transition to a uniform pixel matrix ensues only during the course of the generation of the resulting CT image. Compared to the procedure, that is likewise possible, of already switching to the uniform pixel matrix in the combining of the segment images belonging to a sub-segment to form a sub-image, this offers the advantage of a reduced memory requirement as well as a reduced calculating outlay.

Regardless of whether the decompression ensues during the course of the combining of segment images to form a sub-image or the combining of sub-images to form a resulting CT image, the pixels of the uniform pixel matrix, in a selectable first operating mode, are acquired by interpolation from the pixels of the uniform pixel matrix. Given selection of a second operating mode, the pixels of the uniform pixel matrix are acquired from the pixels of the non-uniform pixel matrix by weighting.

As a result of the alignment of the non-uniform pixel matrix corresponding to the reference projection direction, the non-uniform pixel matrix must be larger than the uniform pixel matrix in both of the just-described operating modes in order, despite the rotation of the non-uniform pixel matrix relative to the uniform pixel matrix, to assure that the non-uniform pixel matrix contains data suitable for the determination of each pixel of the uniform pixel matrix. In the case of a quadratic uniform pixel matrix and a likewise quadratic non-uniform pixel matrix, this means that the side length (for arbitrary reference projection directions) of the non-uniform pixel matrix must be greater than that of the uniform pixel matrix.

As to the procedure in the data decompression by means of interpolation or weighting, the discussion above in conjunction with the combining of a number of segment images to form a sub-image applies analogously, i.e. the averaging also can ensue weighted.

In the described exemplary embodiment, the data compression ensues on the basis of the employment of a non-uniform pixel matrix. Alternatively, other compression methods standard in the field of image processing can be applied.

Figure 7:
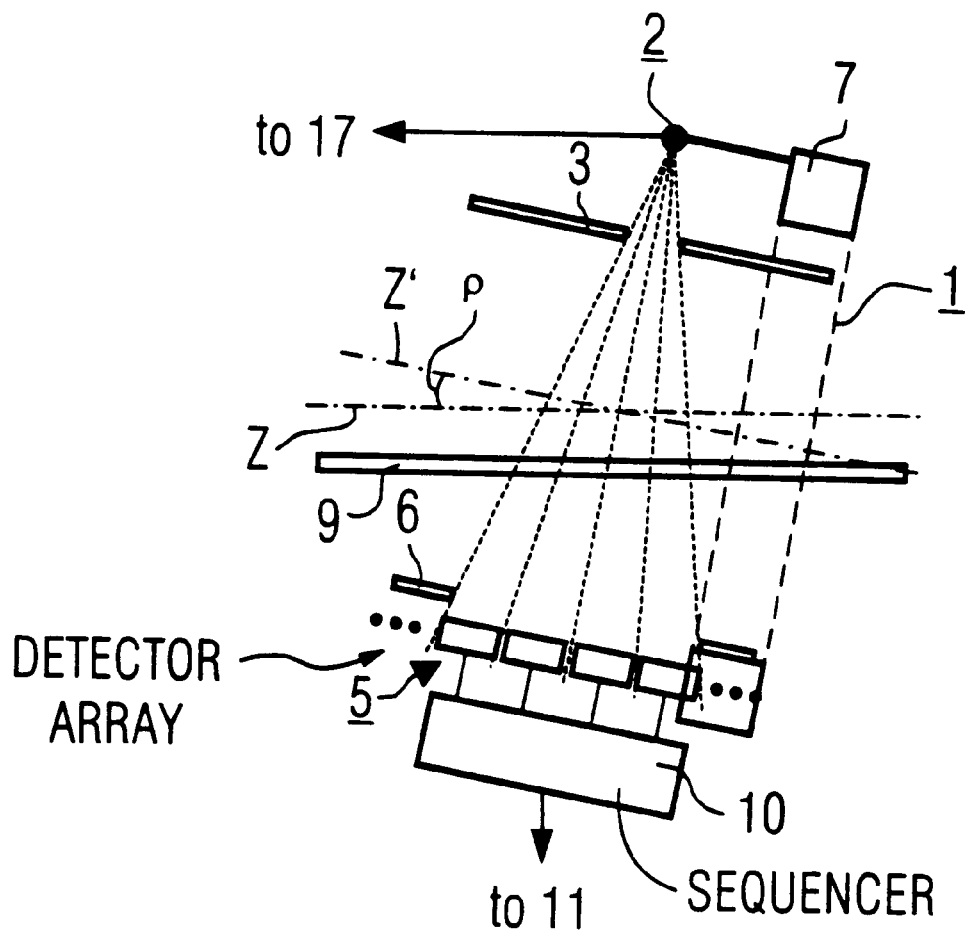
FIG. 7 shows another operating mode of the CT apparatus according to FIGS. 1 and 2 in an illustration analogous to FIG. 2.

In an operating mode with inclined rotary frame 7 illustrated in FIG. 7, the rotational axis Z' around which the focus F rotates around the system axis Z is not identical with the system axis Z but intersects this at the gantry angle ρ. Then the geometry according to FIG. 2 yields a tilted coordinate system according to FIG. 7 with the z'-axis corresponding to the middle axis of the spiral path S that is tilted relative to the z-axis by the gantry angle ρ, with the y'-axis that is likewise tilted by the gantry angle ρ relative to the y-axis, and with the x-axis retained unmodified.

The following is valid for the spiral path S in this coordinate system:

$$\vec{x}'_f = \begin{pmatrix} -R_f\cos\alpha \\ -R_f\sin\alpha + Sp\dfrac{\alpha\sin\rho}{2\pi} \\ Sp\dfrac{\alpha\cos\rho}{2\pi} \end{pmatrix} \quad (15)$$

The above-described procedure for determining the maximum tilt angle $\delta_{max}$ can be transferred to the case of the tilted gantry, whereby the following is valid instead of Equation (6):

$$z'_{Det}(b) = z'(b) - Sp\dfrac{\alpha\cos\rho}{2\pi} \quad (16)$$

$$= -R_f\dfrac{\tan\delta}{\cos\gamma} - Sp\dfrac{\alpha\cos\alpha}{2\pi} - b\left(\sin\alpha\dfrac{\tan\delta}{\cos\gamma} + \cos\alpha\tan\gamma\right),$$

The following is derived therefrom for b=±RFOV:

$$z'_{Det}(=\pm RFOV) = \pm\dfrac{WM}{2}\sqrt{1 - \left(\dfrac{b}{R_f}\right)^2} + \alpha\sin\dfrac{b}{R_f}Sp\dfrac{\cos\alpha}{2\pi} \quad (17)$$

The inclination angle γ' in the coordinate system (x,y',z') for the case of the inclined gantry, however, is now to be introduced into the definition equation for the maximum tilt angle $\delta_{max}$, i.e. into Equation (9).

The following is valid for the inclination angle $\gamma'$ in the case of the inclined gantry:

$$\tan\gamma' = \partial z \frac{\partial z'}{\partial s} = \frac{\partial z'}{\partial \alpha} \cdot \frac{\partial \alpha}{\partial s} \qquad (18)$$

$$= \frac{Sp \cdot \cos\rho}{\sqrt{4\pi^2 \cdot R_f + S^2 p^2 + 4\pi \cdot R_f \cos\alpha \sin\rho \cdot Sp}}$$

or $$\gamma' = \arctan \frac{S\rho \cdot \cos\rho}{\sqrt{4\pi^2 \cdot R_f + S^2 p^2 + 4\pi \cdot R_f \cos\alpha \sin\rho \cdot Sp}}$$

It has been found that the inclination angle $\gamma'$ for the case of the tilted gantry is nearly independent of the reference projection angle $\alpha_r$. It was also found with respect to the maximum tilt angle $\delta_{max}$ that this is nearly independent of the reference projection angle $\alpha_r$.

There is also the possibility in the case of the inclined gantry of determining the appertaining optimum value for the inclination value $\gamma'$ for a given amount of the maximum value of the tilt angle $|\delta_{max}|$ that, for example, is acquired from (9) on the basis of the result acquired according to (18) from the slope of the spiral path S in such a way that an error criterion is met, for example the minimum average of the squares of the distances measured in z-direction of all points of the sub-segment from the image plane.

In the described exemplary embodiment, the relative motion between the measuring unit 1 and the support mechanism 9 is generated by displacing the support mechanism 9. However, there is also the possibility within the framework of the invention of leaving the support mechanism 9 stationary and instead displacing the measuring unit 1. Within the framework of the invention, there is also the possibility of generating the necessary relative motion by displacing both the measuring unit 1 as well as the support mechanism 9.

The conical x-ray beam in the described exemplary embodiment has a rectangular cross-section. In the framework of the invention, however, other cross-sectional geometries are also possible.

A CT apparatus of the third generation was described in conjunction with the above-described exemplary embodiments, i.e. the x-ray source and the detector system are displaced in common around the system axis during the image generation. The invention, however, also can be employed in conjunction with CT apparatuses of the fourth generation wherein only the x-ray source is displaced around the system axis and interacts with a fixed detector ring, insofar as the detector system is a matter of a multi-line array of detector elements.

The inventive method also can be employed with CT apparatuses of the fifth generation, i.e. a CT apparatus wherein the x-radiation emanates from not only one focus but from a number of foci of one or more x-ray sources displaced around the system axis, insofar as the detector system comprises a multi-line array of detector elements.

The CT apparatus employed in conjunction with the above-described exemplary embodiments have a detector system with detector elements arranged in the fashion of an orthogonal matrix. The invention, however, also can be employed in conjunction with CT apparatus having a detector system with detector elements arranged in a planar array or in some other way.

The above-described exemplary embodiments relate to the medical application of the inventive method. The invention, however, also can be employed beyond medicine, for example in baggage inspection or when investigating materials.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for producing a computed tomography (CT) image comprising the steps of:

(a) scanning a subject with a conical x-ray beam emanating from a focus and detecting said beam, after attenuation by said subject, with a matrix-like detector array while moving said focus along a spiral path around said subject relative to a system axis, said detector array generating output data dependent on radiation from said x-ray beam that is incident thereon;

(b) dividing said output data, for a segment of said spiral path having a length adequate for reconstructing a CT image, into a plurality of datasets respectively for a plurality of sub-segments of said segment, each of said sub-segments having a length shorter than said length adequate for reconstructing a CT image;

(c) for each of said sub-segments, reconstructing a plurality of segment images having a plane inclined relative to said system axis from the dataset for that sub-segment;

(d) for each of said sub-segments, combining the plurality of segment images reconstructed from the dataset for that sub-segment to form a partial image with respect to a target image plane; and (e) combining the respective partial images for the respective sub-segments to form a resulting CT image with respect to said target plane.

2. A method as claimed in claim 1 wherein step (c) comprises, for each of said sub-segments, reconstructing a plurality of said segment images in image planes that are inclined relative to both a first axis, that intersects said system axis at a right angle by an inclination angle $\gamma$, and a second axis intersecting each of said first axis and said system axis at respective right angles by a tilt angle $\delta$ measured with respect to said system axis.

3. A method as claimed in claim 1 wherein step (b) comprises dividing said output data into sub-segments wherein neighboring sub-segments overlap in overlapping regions, and comprising the additional step of weighting the output data in said overlap regions so that the respective portions of the output data in said overlap regions belonging to the neighboring sub-segments in that overlap region have respective weightings which, in combination, add to one.

4. A method as claimed in claim 1 wherein step (c) comprises, for each of said sub-segments, reconstructing a plurality of segment images inclined relative to said system axis which have different positions along a z-axis of a Cartesian coordinate system.

5. A method as claimed in claim 4 wherein step (c) further comprises, for each of sub-segments, reconstructing a plurality of images respectively in inclined image planes that intersect in a straight line proceeding tangentially relative to that sub-segment, as said plurality of segment images having a plane inclined relative to said system axis.

6. A method as claimed in claim 4 wherein step (c) comprises, for each of said sub-segments, reconstructing a plurality of said segment images in image planes that are inclined relative to both a first axis, that intersects said system axis at a right angle by an inclination angle γ, and a second axis intersecting each of said first axis and said system axis at respective right angles by a tilt angle δ measured with respect to said system axis, and wherein, in step (c), for each of said sub-segments, the plurality of segment images associated therewith respectively have image planes inclined relative to said system axis limited by extreme values +δ$_{max}$ and −δ$_{max}$ of said tilt angle δ, according to $$\pm\delta_{\max} = \arctan\left(\frac{-\frac{WM}{2} + Sp\frac{\alpha_1}{2\pi} \pm RFOV\cos\alpha_1\tan\gamma_0}{-\frac{R_f}{\cos\gamma_0} - (\pm RFOV)\frac{\sin\alpha_1}{\cos\gamma_0}}\right) \text{ wherein}$$

$$\gamma_0 = \arctan\left(\frac{-Sp\hat{\alpha}}{2\pi R_f \sin\hat{\alpha}}\right).$$

7. A method as claimed in claim 1 wherein step (a) comprises rotating said focus around a rotational axis that coincides with said system axis.

8. A method as claimed in claim 1 wherein step (a) comprises rotating said focus around a rotational axis that intersects said system axis at a gantry angle ρ and wherein, in step (c), for each of said sub-segments, the plurality of segment images have respective inclination angles γ' according to $$\gamma' = \arctan\frac{Sp \cdot \cos\rho}{\sqrt{4\pi^2 \cdot R_f + S^2 p^2 + 4\pi \cdot R_f \cos\alpha\sin\rho \cdot Sp}}.$$

9. A method as claimed in claim 8 wherein step (c) comprises, for each of said sub-segments, reconstructing a plurality of said segment images in image planes that are inclined relative to both a first axis, that intersects said system axis at a right angle by an inclination angle γ, and a second axis intersecting each of said first axis and said system axis at respective right angles by a tilt angle δ measured with respect to said system axis, and wherein, in step (c), for each of said sub-segments, the plurality of segment images associated therewith respectively have image planes inclined relative to said system axis limited by extreme values +δ$_{max}$ and −δ$_{max}$ of said tilt angle δ, according to $$\pm\delta_{\max} = \arctan\left(\frac{-\frac{WM}{2} + Sp\frac{\alpha_1}{2\pi} \pm RFOV\cos\alpha_1\tan\gamma_0}{-\frac{R_f}{\cos\gamma_0} - (\pm RFOV)\frac{\sin\alpha_1}{\cos\gamma_0}}\right) \text{ wherein}$$

$$\gamma_0 = \arctan\left(\frac{-Sp\hat{\alpha}}{2\pi R_f \sin\hat{\alpha}}\right),$$

and further comprising determining an optimum value γ$_{min}$ of said inclination angle γ' for a magnitude of said maximum value of said tilt angle |δ$_{max}$| by satisfying an error criterion.

10. A method as claimed in claim 1 wherein step (c) comprises, for each of said sub-segments, reconstructing a plurality n$_{ima}$ of segment images inclined relative to said system axis which have different positions along a z-axis of a Cartesian coordinate system, and wherein:

$$n_{ima} = \text{floor}\left[\frac{sM}{p}\right]$$

wherein s is a length of the sub-segment.

11. A method as claimed in claim 10 wherein step (c) comprises, for each of said sub-segments, reconstructing a plurality of said segment images in image planes that are inclined relative to both a first axis, that intersects said system axis at a right angle by an inclination angle γ, and a second axis intersecting each of said first axis and said system axis at respective right angles by a tilt angle δ measured with respect to said system axis, and wherein, in step (c), for each of said sub-segments, the plurality of segment images associated therewith respectively have image planes inclined relative to said system axis limited by extreme values +δ$_{max}$ and −δ$_{max}$ of said tilt angle δ, according to $$\pm\delta_{\max} = \arctan\left(\frac{-\frac{WM}{2} + Sp\frac{\alpha_1}{2\pi} \pm RFOV\cos\alpha_1\tan\gamma_0}{-\frac{R_f}{\cos\gamma_0} - (\pm RFOV)\frac{\sin\alpha_1}{\cos\gamma_0}}\right) \text{ wherein}$$

$$\gamma_0 = \arctan\left(\frac{-Sp\hat{\alpha}}{2\pi R_f \sin\hat{\alpha}}\right)$$

and further comprising determining the respective tilt angles δ of the inclined image planes according to $$\delta(i) = \delta_{\max}\frac{2i - (n_{ima} - 1)}{n_{ima} - 1}.$$

12. A method as claimed in claim 1 wherein step (d) comprises, for each of said sub-segments, combining said plurality of segment images by interpolation to form said partial image.

13. A method as claimed in claim 1 wherein step (d) comprises, for each of said sub-segments, combining said plurality of segment images by averaging to form said partial image.

14. A method as claimed in claim 1 wherein step (d) comprises, for each of said sub-segments, combining said plurality of segment images by weighted averaging to form said partial image.

15. A method as claimed in claim 14 wherein step (d) further comprises, for each of said sub-segments, weighting the plurality of segment images for that sub-segment dependent on a predetermined reconstruction slice thickness of said partial image.

16. A method as claimed in claim 1 wherein step (d) comprises, for each sub-segment, selecting said plurality of segment images for combining to form said partial image dependent on a predetermined reconstruction slice thickness of said partial image.

17. A method as claimed in claim 16 wherein step (c) comprises, for each of said sub-segments, reconstructing the segment images with a smallest possible value of said slice thickness of said partial image.

18. A method as claimed in claim 16 wherein step (c) comprises, for each of said sub-segments, selecting said plurality of images to be combined for generating said partial image, according to:

$$N_M = 2 \cdot \max(z^*, \sup_\phi \Delta Z_R) W \cdot N_S.$$

19. A method as claimed in claim 1 comprising the additional step of selecting said target image plane as a plane that intersects said system axis at a right angle.

20. A method as claimed in claim 1 wherein step (e) comprises combining said partial images by addition to form said resulting CT image.

21. A method as claimed in claim 20 wherein each of said segment images has segment image data associated therewith, and comprising the additional step of compressing said segment image data to form compressed data.

22. A method as claimed in claim 21 wherein the step of compressing said segment image data comprises compressing said segment image data to form compressed data exhibiting a non-uniform pixel matrix having resolution in a first direction, proceeding substantially in a direction of a reference projection for the respective sub-segment is higher than in a second direction proceeding substantially orthogonally relative to said reference projection direction.

23. A method as claimed in claim 22 comprising forming said compressed data of pixels having an oblong shape, with each pixel having a longest extent proceeding substantially in said direction of said reference projection direction for that sub-segment.

24. A method as claimed in claim 23 comprising forming said compressed data of rectangular pixels.

25. A method as claimed in claim 23 comprising converting said segment images into said non-uniform pixel matrix.

26. A method as claimed in claim 23 comprising reconstructing said segment images in said non-uniform pixel matrix.

27. A method as claimed in claim 26 wherein said reconstruction of said segment images ensues by back projection in a back-projection direction, and selecting said back-projection direction to substantially coincide with said reference projection direction for that sub-segment.

28. A method as claimed in claim 21 comprising reversing said compression in step (e) to produce said resulting CT image with a uniform pixel matrix.

29. A method as claimed in claim 28 comprising obtaining said pixels of said uniform matrix by interpolation from the pixels of said non-uniform pixel matrix.

30. A method as claimed in claim 28 comprising obtaining said pixels of said uniform matrix by averaging from the pixels of said non-uniform pixel matrix.

31. A computed tomography (CT) apparatus comprising:
a CT scanner having an x-ray source with a focus and a matrix-like detector array for scanning a subject with a conical x-ray beam emanating from said focus and detecting said beam, after attenuation by said subject, with said matrix-like detector array while moving said focus along a spiral path around said subject relative to a system axis, said detector array generating output data dependent on radiation from said x-ray beam that is incident thereon;
a computer supplied with said output data, said computer dividing said output data, for a segment of said spiral path having a length adequate for reconstructing a CT image, into a plurality of datasets respectively for a plurality of sub-segments of said segment, each of said sub-segments having a length shorter than said length adequate for reconstructing a CT image;
said computer, for each of said sub-segments, reconstructing a plurality of segment images having a plane inclined relative to said system axis from the dataset for that sub-segment;
said computer, for each of said sub-segments, combining the plurality of segment images reconstructed from the dataset for that sub-segment to form a partial image with respect to a target image plane; and
said computer, combining the respective partial images for the respective sub-segments to form a resulting CT image with respect to said target plane.

32. A computed tomography apparatus as claimed in claim 31 wherein sai computer, for each of said sub-segments, reconstructs a plurality of said segment images in image planes that are inclined relative to both a first axis, that intersects said system axis at a right angle by an inclination angle $\gamma$, and a second axis intersecting each of said first axis and said system axis at respective right angles by a tilt angle $\delta$ measured with respect to said system axis.

33. A computed tomography apparatus as claimed in claim 31 wherein said computer divides said output data into sub-segments wherein neighboring sub-segments overlap in overlapping regions, and weighs the output data in said overlap regions so that the respective portions of the output data in said overlap regions belonging to the neighboring sub-segments in that overlap region have respective weightings which, in combination, add to one.

34. A computed tomography apparatus as claimed in claim 31 wherein said computer, for each of said sub-segments, reconstructs a plurality of segment images inclined relative to said system axis which have different positions along a z-axis of a Cartesian coordinate system.

35. A computed tomography apparatus as claimed in claim 34 wherein said computer, for each of sub-segments, reconstructs a plurality of images respectively in inclined image planes that intersect in a straight line proceeding tangentially relative to that sub-segment, as said plurality of segment images having a plane inclined relative to said system axis.

36. A computed tomography apparatus as claimed in claim 34 wherein said computer, for each of said sub-segments, reconstructs a plurality of said segment images in image planes that are inclined relative to both a first axis, that intersects said system axis at a right angle by an inclination angle $\gamma$, and a second axis intersecting each of said first axis and said system axis at respective right angles by a tilt angle $\delta$ measured with respect to said system axis, and wherein, for each of said sub-segments, the plurality of segment images associated therewith respectively have image planes inclined relative to said system axis limited by extreme values $+\delta_{max}$ and $-\delta_{max}$ of said tilt angle $\delta$, according to $$\pm \delta_{\max} = \arctan\left(\frac{-\frac{WM}{2} + Sp\frac{\alpha_1}{2\pi} \pm RFOV\cos\alpha_1\tan\gamma_0}{-\frac{R_f}{\cos\gamma_0} - (\pm RFOV)\frac{\sin\alpha_1}{\cos\gamma_0}}\right) \text{ wherein}$$

$$\gamma_0 = \arctan\left(\frac{-Sp\hat{\alpha}}{2\pi R_f \sin\hat{\alpha}}\right).$$

37. A computed tomography apparatus as claimed in claim 31 wherein said focus rotates around a rotational axis that coincides with said system axis.

38. A computed tomography apparatus as claimed in claim 31 wherein said focus rotates around a rotational axis that intersects said system axis at a gantry angle $\rho$ and wherein, for each of said sub-segments, the plurality of segment images have respective inclination angles $\gamma'$ according to $$\gamma' = \arctan\frac{Sp\cdot\cos\rho}{\sqrt{4\pi^2\cdot R_f + S^2 p^2 + 4\pi\cdot R_f \cos\alpha\sin\rho\cdot Sp}}.$$

39. A computed tomography apparatus as claimed in claim 38 wherein said computer, for each of said sub-segments, reconstructs a plurality of said segment images in image planes that are inclined relative to both a first axis, that intersects said system axis at a right angle by an inclination angle γ, and a second axis intersecting each of said first axis and said system axis at respective right angles by a tilt angle δ measured with respect to said system axis, and wherein, for each of said sub-segments, the plurality of segment images associated therewith respectively have image planes inclined relative to said system axis limited by extreme values $+\delta_{max}$ and $-\delta_{max}$ of said tilt angle δ, according to $$\pm\delta_{max} = \arctan\left(\frac{-\frac{WM}{2} + Sp\frac{\alpha_1}{2\pi} \pm RFOV\cos\alpha_1\tan\gamma_0}{-\frac{R_f}{\cos\gamma_0} - (\pm RFOV)\frac{\sin\alpha_1}{\cos\gamma_0}}\right) \text{ wherein}$$

$$\gamma_0 = \arctan\left(\frac{-Sp\hat{\alpha}}{2\pi R_f \sin\hat{\alpha}}\right),$$

and further comprising determining an optimum value $\epsilon_{min}$. Of said inclination angle γ' for a magnitude of said maximum value of said tilt angle $|\delta_{max}|$ by satisfying an error criterion.

40. A computed tomography apparatus as claimed in claim 31 wherein said computer, for each of said sub-segments, reconstructs a plurality $n_{ima}$ of segment images inclined relative to said system axis which have different positions along a z-axis of a Cartesian coordinate system, and wherein:

$$n_{ima} = \text{floor}\left[\frac{sM}{p}\right]$$

wherein s is a length of the sub-segment.

41. A computed tomography apparatus as claimed in claim 40 wherein said computer, for each of said sub-segments, reconstructing a plurality of said segment images in image planes that are inclined relative to both a first axis, that intersects said system axis at a right angle by an inclination angle γ, and a second axis intersecting each of said first axis and said system axis at respective right angles by a tilt angle δ measured with respect to said system axis, and wherein, for each of said sub-segments, the plurality of segment images associated therewith respectively have image planes inclined relative to said system axis limited by extreme values $+\delta_{max}$ and $-\delta_{max}$ of said tilt angle δ, according to $$\pm\delta_{max} = \arctan\left(\frac{-\frac{WM}{2} + Sp\frac{\alpha_1}{2\pi} \pm RFOV\cos\alpha_1\tan\gamma_0}{-\frac{R_f}{\cos\gamma_0} - (\pm RFOV)\frac{\sin\alpha_1}{\cos\gamma_0}}\right)$$

wherein $$\gamma_0 = \arctan\left(\frac{-Sp\hat{\alpha}}{2\pi R_f \sin\hat{\alpha}}\right)$$

and further comprising determining the respective tilt angles δ of the inclined image planes according to $$\delta(i) = \delta_{max}\frac{2i - (n_{ima} - 1)}{n_{ima} - 1}.$$

42. A computed tomography apparatus as claimed in claim 31 wherein said computer, for each of said sub-segments, combines said plurality of segment images by interpolation to form said partial image.

43. A computed tomography apparatus as claimed in claim 31 wherein said computer, for each of said sub-segments, combines said plurality of segment images by averaging to form said partial image.

44. A computed tomography apparatus as claimed in claim 31 wherein said computer, for each of said sub-segments, combines said plurality of segment images by weighted averaging to form said partial image.

45. A computed tomography apparatus as claimed in claim 44 wherein said computer, for each of said sub-segments, weighs the plurality of segment images for that sub-segment dependent on a predetermined reconstruction slice thickness of said partial image.

46. A computed tomography apparatus as claimed in claim 31 wherein said computer, for each sub-segment, selects said plurality of segment images for combining to form said partial image dependent on a predetermined reconstruction slice thickness of said partial image.

47. A computed tomography apparatus as claimed in claim 46 wherein said computer, for each of said sub-segments, reconstructs the segment images with a smallest possible value of said slice thickness of said partial image.

48. A computed tomography apparatus as claimed in claim 46 wherein said computer, for each of said sub-segments, selects said plurality of images to be combined for generating said partial image according to:

$$N_M = 2\cdot\max(z^*, \sup\phi\Delta z_R) W\cdot N_S.$$

49. A computed tomography apparatus as claimed in claim 31 wherein said computer selects said target image plane as a plane that intersects said system axis at a right angle.

50. A computed tomography apparatus as claimed in claim 31 wherein said computer combines said partial images by addition to form said resulting CT image.

51. A computed tomography apparatus as claimed in claim 50 wherein each of said segment images has segment image data associated therewith, and wherein said computer has a compression stage compressing said segment image data to form compressed data.

52. A computed tomography apparatus as claimed in claim 51 wherein said compression stage compresses said segment image data to form compressed data exhibiting a non-uniform pixel matrix having resolution in a first direction, proceeding substantially in a direction of a reference projection for the respective sub-segment is higher than in a second direction proceeding substantially orthogonally relative to said reference projection direction.

53. A computed tomography apparatus as claimed in claim 52 wherein said compression stage forms said compressed data of pixels having an oblong shape, with each pixel having a longest extent proceeding substantially in said direction of said reference projection direction for that sub-segment.

54. A computed tomography apparatus as claimed in claim 53 wherein said compression stage forms said compressed data of rectangular pixels.

55. A computed tomography apparatus as claimed in claim 53 wherein said computer converts said segment images into said non-uniform pixel matrix.

56. A computed tomography apparatus as claimed in claim 53 wherein said computer reconstructs said segment images in said non-uniform pixel matrix.

57. A computed tomography apparatus as claimed in claim 56 wherein said computer reconstructs said segment images ensues by back projection in a back-projection direction, and selects said back-projection direction to substantially coincide with said reference projection direction for that sub-segment.

58. A computed tomography apparatus as claimed in claim 51 wherein said computer reverses said compression to produce said resulting CT image with a uniform pixel matrix.

59. A computed tomography apparatus as claimed in claim 58 wherein said computer obtains said pixels of said uniform matrix by interpolation from the pixels of said non-uniform pixel matrix.

60. A computed tomography apparatus as claimed in claim 58 wherein said computer obtains said pixels of said uniform matrix by averaging from the pixels of said non-uniform pixel matrix.

* * * * *